United States Patent
Kulik et al.

(10) Patent No.: US 9,360,406 B2
(45) Date of Patent: Jun. 7, 2016

(54) METHOD AND APPARATUS FOR SELF-CALIBRATION OF DENSITY PROFILER

(71) Applicant: Thermo Fisher Scientific Inc., Sugar Land, TX (US)

(72) Inventors: Alex Kulik, Sugar Land, TX (US); Michael George Brosseau, Stafford, TX (US); Hai Wang, Sugar Land, TX (US)

(73) Assignee: Thermo Fisher Scientific Inc., Sugar Land, TX (US)

( * ) Notice: Subject to any disclaimer, the term of this patent is extended or adjusted under 35 U.S.C. 154(b) by 558 days.

(21) Appl. No.: 13/864,459

(22) Filed: Apr. 17, 2013

(65) Prior Publication Data
US 2014/0316734 A1 Oct. 23, 2014

(51) Int. Cl.
G01F 1/12 (2006.01)
G01F 25/00 (2006.01)
G01N 9/00 (2006.01)
G01N 9/24 (2006.01)

(52) U.S. Cl.
CPC ... *G01N 9/00* (2013.01); *G01N 9/24* (2013.01)

(58) Field of Classification Search
CPC .... G01N 9/00; G01N 2223/601; G01F 25/00; G01F 1/363; G01F 25/0007; G01F 25/0038; G01F 15/02
USPC ................................. 702/100; 73/1.16, 1.35
See application file for complete search history.

(56) References Cited

U.S. PATENT DOCUMENTS

| | | | |
|---|---|---|---|
| 4,197,462 A | 4/1980 | Kopp | |
| 6,879,425 B2* | 4/2005 | Damm | G01F 23/288 164/454 |
| 7,469,033 B2 | 12/2008 | Kulik et al. | |
| 7,492,859 B2* | 2/2009 | Kulik | G01N 9/24 378/54 |
| 8,306,187 B2 | 11/2012 | Kulik et al. | |
| 8,370,098 B2* | 2/2013 | Hocker | G01F 1/36 702/100 |
| 2004/0200259 A1* | 10/2004 | Mattar | G01F 1/74 73/1.34 |
| 2008/0112536 A1 | 5/2008 | Kulik et al. | |

FOREIGN PATENT DOCUMENTS

| | | |
|---|---|---|
| CN | 101796386 A | 8/2010 |
| GB | 2326232 A | 12/1998 |
| GB | 2496746 A | 5/2013 |
| JP | 11014437 A | 1/1999 |

OTHER PUBLICATIONS

Combined Search and Examination Report issued Sep. 29, 2014 in corresponding United Kingdom application No. GB1406560.1 (5 pages).

* cited by examiner

*Primary Examiner* — An Do
(74) *Attorney, Agent, or Firm* — William R. McCarthy, III

(57) ABSTRACT

A process and system for self-calibration of a density profiler is disclosed. The process may include measuring a density profile of a fluid in a vessel using a plurality of sensors or a single sensor, and measuring a density profile of the fluid in the vessel using a plurality of sample ports. A density of the fluid proximate a location of at least one of the plurality of sample ports based on the sensor measured density profile may then be interpolated. A density of the fluid proximate a location of at least one of the plurality of sensors based on the sample port measured density profile may also be interpolated. Adjustment of a calibration of at least one of the plurality of sensors may then be made based on both the interpolated sample port density and the interpolated sensor density.

16 Claims, 6 Drawing Sheets

METHOD AND APPARATUS FOR SELF-CALIBRATION OF DENSITY PROFILER

FIELD OF THE DISCLOSURE

Embodiments disclosed herein relate generally to a density profiler. More specifically, embodiments disclosed herein relate to a method and apparatus for self-calibration of a density profiler.

BACKGROUND

The petroleum industry is generally categorized into three parts: upstream, midstream, and downstream. Upstream processes are generally considered to be the processes that are conducted in the oilfield and are most commonly used to refer to the processes of searching for and recovering crude oil and/or natural gas from the Earth. Crude oil is a fossil fuel containing hydrocarbons and other organic liquids and is most commonly found below the Earth's surface. Typically, as it is difficult to separate during extraction, crude oil is obtained with many other fluids found below the Earth's surface, including water and gases. Initial separations at the oilfield may be used to separate the water, oil, and gases based on density differences, such as via settling tanks and other vessels or process equipment. The extracted crude oil is then processed and refined into useful and more valuable products such as diesel fuel, gasoline, kerosene, etc.

The processing and refining of crude oil is conducted at an oil refinery and is an essential part of the downstream side of the petroleum industry. During the refining process, the hydrocarbons may be processes in mixture with gases, solids, and or other liquids, including water. While in a storage or process vessel, the process fluid(s) may undergo stratification (layering) under the natural force of gravity due to the varying densities of the different substances that make up the process fluid in the vessel. Additionally, in certain processes, an electric field may be applied to the process fluid of the vessel in order to facilitate stratification. The facilitation using an electric field is known as electrophoresis.

Due to the different amounts of crude oil, water, and any other liquids or gases in the process mixtures, at the oilfield, during refining, etc., the layering of the fluids in the vessel is not consistent or constant. Therefore, as the processing may be continuous and ongoing, it is difficult to determine the density profile (i.e., the density of the process fluid contained within the vessel at several elevations along the vessel simultaneously) of the process fluid at any given time.

In many cases, however, it is beneficial to know the density profile of the process fluid at a specific time. Engineers use the density information to determine the percentages of each liquid contained within the process fluid, completeness of separations, etc. In addition, engineers may also use the density profile information to make adjustments to the refining process, control flows to and from vessels, and control of other aspects of the processes. Further, it is important for productivity and quality to know water, oil, and emulsion (mixture) are located within the vessel at any given time. To determine the density profile in a vessel, process vessels may be equipped with a number of sampling ports (taps). Typically, the taps may be disposed at different elevations along the wall of the vessel.

Using the taps, obtaining samples of the process fluid at each tap elevation is convenient. However, taking a sample from each tap and analyzing each sample in the lab is laborious and slow. Therefore, by the time each sample is analyzed in the lab and the density at each elevation is calculated, there may no longer be a need for the density profile information. As such, it may be advantageous and more efficient to employ an array of sensors where each sensor is capable of calculating the density of the process fluid at a particular elevation at any given time.

Like most sensing and measuring tools, each sensor of the sensor array needs to be properly calibrated. Calibration is necessary in order to determine both the accuracy of each sensor's response and, more importantly, to maintain the accuracy of each sensor's measurements. One useful and common method to calibrate the sensor array is done by using a two-point calibration technique. In this technique, the vessel is successively filled with two liquids of different and known densities, for example, water and oil. Afterwards, the response of each sensor in the sensor array is recorded and memorized. Typically, it is beneficial to fill the vessel with liquids whose densities vary greatly between each another. In this respect, the measurement of each liquid will likely result in vastly different sensor responses. Therefore, the change in density that the sensor detects will be much more noticeable in each sensor's response. In operation, the density at specific elevations may then be derived from each sensor's response by interpolating between the densities used in calibration of the sensor array to resulting in a calculated density based on the sensor's response.

Despite the simplicity of the aforementioned two-point calibration or re-calibration technique, it is unpopular in the refining process as it is disruptive to production as production would need to be stopped in order to fill the vessel successively with two liquids of known densities. As mentioned above, it is beneficial and, in most cases, preferred, to have an uninterrupted refinement process. Therefore, process engineers need a method to calibrate or re-calibrate each sensor of the sensor array without halting production.

SUMMARY OF THE CLAIMED EMBODIMENTS

In one aspect, embodiments disclosed herein relate to a process for self-calibration of a density profiler. The process may include measuring a density profile of a fluid in a vessel using a plurality of sensors or a single sensor, and measuring a density profile of the fluid in the vessel using a plurality of sample ports. A density of the fluid proximate a location of at least one of the plurality of sample ports based on the sensor measured density profile may then be interpolated. A density of the fluid proximate a location of at least one of the plurality of sensors based on the sample port measured density profile may also be interpolated. Adjustment of a calibration of at least one of the plurality of sensors may then be made based on both the interpolated sample port density and the interpolated sensor density.

In another aspect, embodiments disclosed herein relate to a system for self-calibration of a density profiler. The system may include: a plurality of sensors for measuring a density profile of a fluid in a vessel; a plurality of sample ports for measuring a density profile of the fluid in the vessel; and a computer system. The computer system may be configured to: interpolate a density of the fluid proximate a location of at least one of the plurality of sample ports based on the sensor measured density profile; interpolate a density of the fluid proximate a location of at least one of the plurality of sensors based on the sample port measured density profile; and adjust a calibration of at least one of the plurality of sensors based on both the interpolated sample port density and the interpolated sensor density.

This summary is provided to introduce a selection of concepts that are further described below in the detailed description. This summary is not intended to identify key or essential features of the claimed subject matter, nor is it intended to be used as an aid in limiting the scope of the claimed subject matter. Other aspects and advantages of the invention will be apparent from the following description and the appended claims.

DETAILED DESCRIPTION

In one aspect, embodiments herein relate to relate generally to a density profiler. More specifically, embodiments disclosed herein relate to a method and apparatus for self-calibration of a density profiler.

Specific embodiments of the present disclosure will be described with reference to the accompanying figures. In the following detailed description of embodiments, numerous specific details are set forth in order to provide a more thorough understanding of the disclosure. However, it will be apparent to one of ordinary skill in the art that the present disclosure may be practiced without these specific details. In other instances, well-known features have not been described in detail to avoid obscuring the disclosure.

As used herein, "fluid" refers to gases, liquids, and solids, or mixtures thereof that may be contained within a vessel. Fluids may include aqueous liquids, organic liquids, single-phase systems, and multi-phase systems such as foams, emulsions, and fluidized particles. As used herein, "density profile" refers to the density of a fluid at a plurality of locations (i.e., as a function of position). For example, a density profile of a fluid within a vessel may include the density of the fluid at several different elevations within the vessel.

Figure 1:
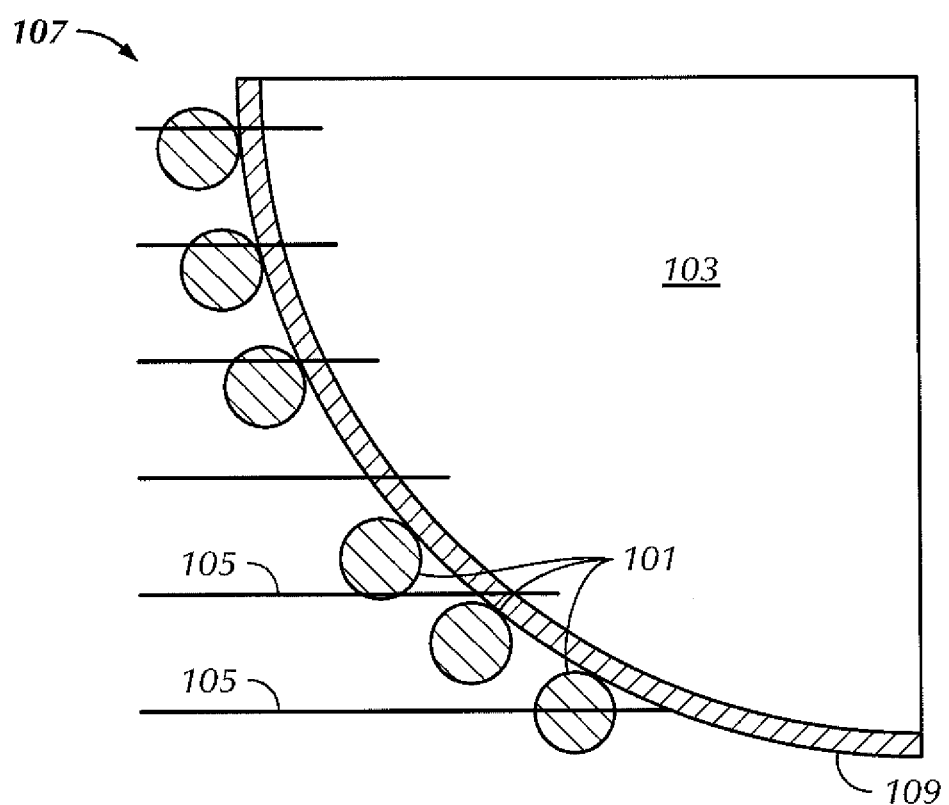
FIG. 1 is a schematic view of a system in accordance with one or more embodiments of the present disclosure.

Referring now to FIG. 1, a schematic diagram of a lower portion of a vessel 109 including a density profiler 107 in accordance with one or more embodiments herein is illustrated. Vessel 109 may be equipped with one or more sample ports 105 located at different elevations. Sample ports 105 may be used to extract samples of the process fluid 103 within the vessel at the different elevations. The samples may then be measured to determine the actual density of the fluid within the vessel proximate the sample ports. The lab or field measured density, along with the known elevation of the sample ports, may be used to determine a density profile of the process fluid within the vessel.

As noted above, lab measurements may require time consuming analyses, as well as manpower for extracting the samples, manpower for measuring the samples, and communicating the sample data to operations. The lab measurements may thus provide a rearward looking density profile which may not reflect the actual density profile in vessel 109 when operations receive the data. This may make process control difficult. Additionally, the lab (not shown) may be located at the same site of the vessel or at a remote location. Further, analyzing the samples obtained from the taps 105 may be performed immediately after a sample has been obtained or at any later time, depending upon the location of the vessel, the particular operation, and the specific process needs.

To facilitate real-time measurement of the density, a density profiler 107 may be used, where density profiler 107 may include two or more sensors 101 for measuring a density of the fluid mixture 103 at different vessel elevations. Sensors 101 may thus provide sensor measurement of the density as a function of elevation (height within the vessel). Sensors 101 may include any type of density measurement devices, and in some embodiments may include gamma ray density measurement devices such as those described in U.S. Pat. Nos. 8,306,187 and 7,469,033 as well as U.S. patent application Ser. Nos. 13/298,155 and 13/650,771 In some embodiments, the density profiler 107 may include a single sensor 101, such as a position sensitive gamma ray detector disposed proximate the vessel, where the single sensor may be used to provide a sensor-measured density profile. Sensors 101 and the sample ports 105 may be located at the same or different elevations along the vessel wall 109 with respect to each other, such as illustrated in FIG. 1.

For example, where the density profiler 107 includes at least one gamma ray detector positioned proximate to a vessel. The gamma ray detector is configured to measure backscattered gamma ray counts and determine the density of the fluid proximate the sensor and contained in the process vessel based on the backscattered gamma ray counts. Both the gamma ray source (not independently illustrated) and the gamma ray detector (not independently illustrated) of sensors 101 may be attached or otherwise mounted near the wall 109 of the vessel.

The gamma-ray source may emit gamma radiation through the vessel wall 109 and into the process fluid 103 which may be gases, liquids, and solids, or mixture thereof, associated with the process. One of ordinary skill will appreciate that the contents of the vessel may be more complex than the simple example shown in FIG. 1. For example, the process fluid 103 may comprise several fluids of differing densities and the fluids may be separated and/or mixed. The emitted gamma radiation may backscatter from the process fluid 103, and the backscattered gamma radiation may be subsequently detected by the gamma ray detector.

The detector produces an electrical pulse in response to a γ-ray, and by counting pulses one would know the flux of γ-rays (how many γ-ray hit the sensor per second). The counting rate N or voltage may then be converted to a density ρ, for example, using the equation: $N = -\alpha\rho + \beta$ where $\alpha$ and $\beta$ are calibration factors. The actual equations used for converting count rates or voltages to densities may be more or less complex, the simplified equation presented herein for illustrative purposes only.

In some embodiments, the density profiler may be installed on a new vessel. For such new construction, the sensors may be initially calibrated using two or more fluids to determine the calibration constants and/or any other necessary offset/calibration values. In other embodiments, a density profiler including multiple sensors 101 may be installed on an operating vessel with a set of initial calibration constants. The set of initial calibration constants may be known, such as from knowledge of the initial system calibration. The constants may be determined from a prioi knowledge of the process fluid 103 or from previously used calibration constants. Further, calibration constants may include values that were estimated in order to provide a starting point (which may be referenced at a later time) for the calibration of the sensors 101 during operation. In either instance, new installation or retrofit, the sensor output may need to be calibrated or re-calibrated so as to provide an accurate measurement of density over the full range of fluids that may be encountered within the vessel. Embodiments disclosed herein provide for self-calibration of the sensors during routine operation of the vessel.

Processes for self-calibration of a density profiler according to embodiments herein require both laboratory (actual) measurement of the density as well as sensor measurements. Although the process fluid 103 may be continuously changing during operation, a constantly changing fluid can be used to collect sets of data. Specifically, samples obtained from the taps 105 may be analyzed to determine the density of the process fluid 103 at the elevation of the tap the sample was obtained from. In addition, and at the same time, sensor data may be acquired from the response of the sensors 101 in the sensor array. Further, analyzing samples obtained from the taps 105 and acquiring the response of the sensors 101 may be performed at several different times throughout operation in order to obtain multiple sets of data corresponding to different times throughout operation. Using multiple data sets is beneficial in order to continuously tune, or calibrate, the response of the sensors 101 in the sensor array and may result in an efficient and accurate determination of the density profile of the process fluid 103. The calibration constants of the sensors may then be adjusted on the fly by training the sensors based on the measured density (actual).

Training of the sensors, however, may not be a simple matter. The density profile in a vessel would normally indicate a transition from a low density at the top of the vessel to a high density proximate the bottom of the vessel. However, empirical modeling that may be used to train the sensors and calculate appropriate calibration constants for the system may have excess degrees of freedom, and minimization of errors may result in overfitting. Overfitting of the model may then result in erroneous density readings for one or more sensors in the density profiler.

Figure 2:
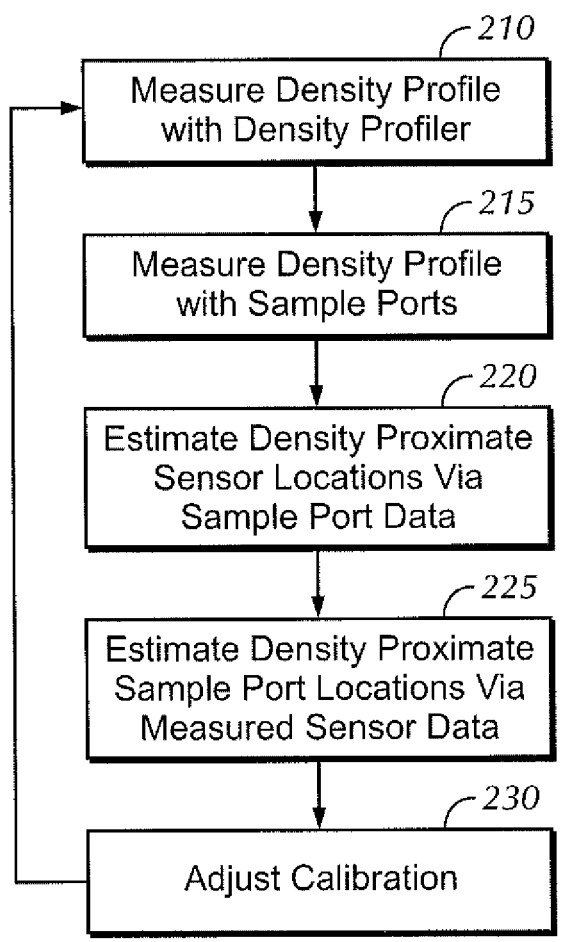
FIG. 2 illustrates a method for self-calibration of a density profiler according to embodiments herein.

To properly calibrate density profilers according to embodiments herein, the calibration process may include the steps as illustrated in FIG. 2. In step 210, the density profile of a fluid in a vessel may be measured using a plurality of sensors. In step 215, the density profile of the fluid in the vessel may be measured using a plurality of sample ports.

A density of the fluid proximate a location of at least one of the plurality of sample ports may be estimated based on the sensor measured density profile in step 220. A density of the fluid proximate a location of at least one of the plurality of sensors may be estimated based on the sample port measured density profile in step 225.

The estimated density at the elevation of each tap 105 may be determined by interpolating between the two sensors whose elevations are adjacent to the tap elevation (preferably, one sensor at a higher elevation and one sensor at a lower elevation with respect to the tap elevation). The interpolated tap densities represent a density at the tap elevation based on the densities determined from the response of each sensor 101. The interpolation between the sensors 101 may be linear, polynomial, any other interpolation known in the art, or any combination thereof. Additionally, one of ordinary skill in the art would know and appreciate that there may not exist a sensor at a higher elevation or a lower elevation with respect to the tap elevation and therefore, other interpolation techniques may be used or the density at the tap elevation may not be interpolated.

Likewise, the estimated density at the elevation of each sensor 101 may be determined by interpolating between two sample port measured densities whose elevations are adjacent to the sensor elevation. The interpolated sensor densities represent a density at the sensor elevation based on the laboratory or actual physical measurement of the density of the fluid as withdrawn from the sample port (proper flushing of sample ports should be used to retrieve a representative sample).

The calibration of at least one of the plurality of sensors may then be adjusted 230 based on both the interpolated sample port density and the interpolated sensor density.

The calibration adjustments to be made in step 230 may be determined in some embodiments by (a) minimizing a first error function based on an initial sensor calibration constant, the measured sample port density profile and the interpolated sample port density to determine a new or current calibration constant; and (b) calculating a second error function based on an initial sensor calibration constant, the measured sensor density profile, the interpolated sensor density, and the determined current calibration constant. The first error function may be iteratively minimized by adjusting the calibration constants to match the sensor density profile to the sample port measured density profile. The second error function may be monitored during the iterative process to minimize the first error function. The iterative process may then be halted upon reaching a minimum in the second error function. The calibration constants determined during the iterative process for one or more of the sensors may then be re-set or adjusted to the new or current calibration constant determined when the second error function reaches a minimum.

In some embodiments, the first error function $L_1$ may be represented by the equation:

$$L_1 = \sum_{p=1}^{n} \sum_{i=1}^{m} \left[ t_{ip}(\vec{s}_0, \vec{C}_0, \vec{C}) - l_{ip} \right]^2$$

where m is a number of sample ports analyzed n times, t is an interpolated sample port density, l is a measured sample port density, $\vec{s}_0$ is an initial sensor density, $\vec{C}_0$ is an initial calibration constant, and $\vec{C}$ is the current calibration constant. $\vec{s}_0$, $\vec{C}_0$ and $\vec{C}$ are all vectors. For example, if there are 6 sensors, then $\vec{s}_0$ is 6 numbers, $\vec{C}_0$ and $\vec{C}$ are 12 numbers each.

The second error function $L_2$ may be represented by the equation:

$$L_2 = \sum_{jp} \left( s_{jp}(\vec{s}_0, \vec{C}, \vec{C}^*) - s_{jp}^* \right)^2$$

where j is a number of sample ports analyzed p times, s is a measured sensor density, s* is an interpolated sensor density, $\vec{s}_0$ is an initial sensor density, $\vec{C}$ is the current calibration constant, and $\vec{C}^*$ is a model calibration constant. $\vec{s}_0$, $\vec{C}_0$ and $\vec{C}$, as for $L_1$, are all vectors. For example, if there are 6 sensors, then $\vec{s}_0$ is 6 numbers, $\vec{C}_0$ and $\vec{C}$ are 12 numbers each.

Self-calibration according to embodiments herein thus requires measurement of actual density data and sensor data.

As laboratory measurements may take time, the training may be based on accumulated historical data. A history of the sensor measured density profile may be stored in a data store for later use in system calibration. The sensor history may include, for example, one or more of a sensor identifier, a sensor location or height, a time stamp, and at least one of an initial sensor calibration constant (initial being the calibration constant associated with the sensor at the time of the time stamp), a sensor voltage counting rate output value, and a sensor density measurement value. Once measured, a history of the sample port measured density profile may be input into the data store. The sample port history may include, for example, one or more of a sample port identifier, a sample port location or height, a sample time stamp, and a measured density value.

Retrieving samples from the vessel may be performed by plant operators at routine times, such as every two, four, or six hours, or other time intervals as may be appropriate to the operation. The "routine" samples, however, may not be withdrawn from the vessel at the specified time interval due to ongoing plant operations; a 4 o'clock sample, for example, may be withdrawn at 3:45 one day and 4:30 the next. Further, the sensor history data may be recorded at intervals that do not correspond to the sample times. Accordingly, embodiments herein may also match a time stamp of the sample port history to a time stamp of the sensor history for use in the calculating and monitoring $L_1$ and $L_2$.

Even after the calibration constants for the sensors are adjusted so as to accurately represent the density of the fluids in the vessel, it may be desired to re-calibrate the sensors. For example, the process may be continuously changing due to its intrinsic reasons. Sensor drift, introduction of new fluids of varying densities into the vessel, vessel, vessel and/or detector aging and other factors may also contribute to the need to update sensor calibration. As such, the steps described above, the measuring a density profile with sensors, the measuring a density profile with sample ports, the minimizing a first error function, and the calculating a second error function, may be repeated as necessary to determine new calibration constants for the plurality of sensors based on newly acquired or recent historical data.

During operations, the density and/or density profile of a fluid in a vessel (i.e., the process density and/or process density profile) may be controlled by manipulating one or more process variables based upon the measured density and/or density profile. For example, where a vessel forms a component in a process, one or more process variables may be manipulated in response to the sensor measured density profile of the fluid in the vessel. The sensor data may be displayed and process variable manipulation may be performed, for example, using a process control system.

In some embodiments, the process control system may be configured to perform the self-calibration of the sensors. For example, the process control system may include software and hardware for storing the historical sensor data, receiving and storing the input sample port data, and determining the updated calibration constants.

In other embodiments, historical sensor data may be exported from or retrieved from the process control system to a remote computer system including hardware and software for storing the historical sensor data, receiving and storing the input sample port data, and determining the updated calibration constants. The updated calibration constants may then be communicated back to or input into the process control system.

Whether self-calibration is performed locally or remotely, or even on a plurality of nodes, the process control system and the remote computer systems may include or be connected to a local area network (LAN), a wide area network (e.g., the internet), as well as other communication and display means such as a keyboard, a network interface connection, monitors (display devices), associated physical memory, shared memory, or other input, output, storage and processing devices and computer readable medium known to those skilled in the art.

As an example of the self-calibration technique described above, suppose there are m taps sampled and analyzed n times, $l_{ip}$; i=1, 2, ..., m; p=1, 2, ..., n and densities reported by sensors $\vec{s}_0$ recorded each time. The subscript "0" is used to emphasize that the densities $\vec{s}_0$ were obtained with initial calibration constants $\vec{C}_0$ effective at the initial sample time. When the calibration constants change, so will the densities reported by the sensors and may be represented by the relationship as function:

$$\vec{S}(\vec{C}) = \vec{s}(\vec{s}_0, \vec{C}_0, \vec{C}).$$

In the simplest case of linear response and mutually independent sensors, the density reported by i-th sensor is $$s_i = C_i^{low} \frac{C_{i,0}^{high} - s_{i,0}}{C_{i,0}^{high} - C_{i,0}^{low}} + C_i^{high} \frac{s_{i,0} - C_{i,0}^{low}}{C_{i,0}^{high} - C_{i,0}^{low}}.$$

The actual relation may be simpler or more than as shown above. Using this relationship, the sensor density may be obtained at any time and while using any set of calibration constants. The densities t at tap elevations may be estimated from s by interpolation, for example. Therefore, at any time, the estimated tap density is a known function of the sensor array readings $\vec{s}_0$, calibration constants at sampling time $\vec{C}_0$, and current calibration constants $\vec{C}$ and may be represented by:

$$\vec{t} = \vec{t}(\vec{s}) = \vec{t}(\vec{s}(\vec{s}_0, \vec{C}_0, \vec{C}))$$

The updated calibration constants may then be determined by minimization of the function:

$$L_1 = \sum_{p=1}^{n} \sum_{i=1}^{m} \left[ t_{ip}(\vec{s}_0, \vec{C}_0, \vec{C}) - l_{ip} \right]^2 \Rightarrow \min$$

versus the vector of calibration constants $\vec{C}$. The sensor array readings and calibration constants at sampling time, $\vec{s}_0$ and $\vec{C}_0$, are known constants and, in addition, $$t_{ip}(\vec{s}_0, \vec{C}_0, \vec{C})$$

is a known function. The sum runs over the taps i and sampling sets p. Minimization can be performed by any of the standard methods, for example, gradient descent. One of ordinary skill in the art would know and appreciate that the aforementioned interpolation, summation, and minimization calculations may be solved by any mathematical method known in the art.

The minimization procedure described above is essentially building an empirical model of sensor response to the density ranges encountered during routine operations. The model is the collection of calibration constants $\vec{C}^*$. In some cases, an issue known as overfitting may occur. Overfitting happens when the model is excessive, i.e., there are more degrees of freedom in the minimization problem than the data actually permit.

Figure 3:
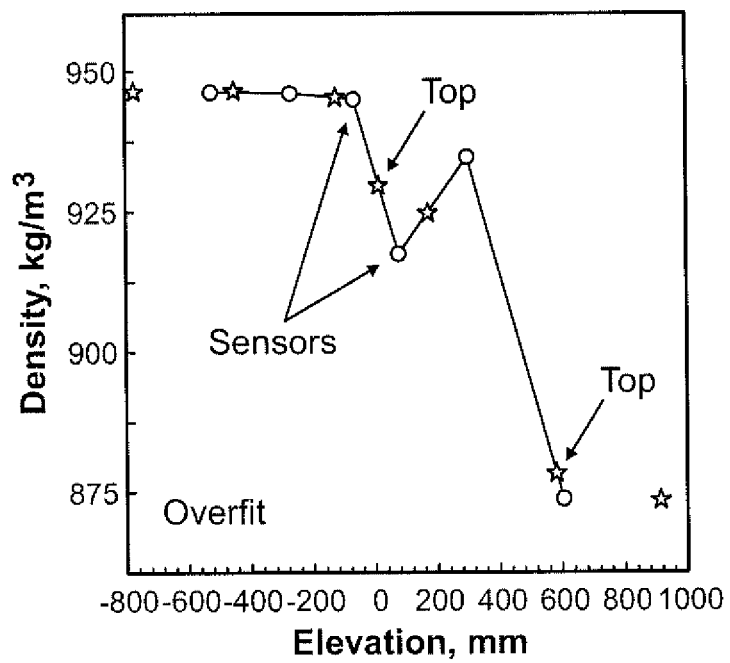
FIGS. 3, 4, and 6 illustrate density plots illustrating self-calibration of a density profiler according to embodiments herein.

To illustrate this, FIG. 3 shows an example of overfitting. Here, the estimated tap densities t (shown as stars in the plot) are obtained by interpolation between the sensors' responses, or nodes (shown as bullets in the plot). By nature, denser substances would be lower in elevation in the vessel with respect to other, less dense substances. Therefore, the estimated tap densities t systematically decrease as the elevation increases. However, as shown in FIG. 3, the interpolation nodes (bullets) illustrate the opposite: counting from lower elevation (or from the left of the plot), the density at the 5-th node is greater than the density at the 4-th node. Although this result achieves the absolute minimum of $L_1$, it is likely to be a feature of the specific dataset used to minimize $L_1$ rather than a general trend of the data.

Figure 4:
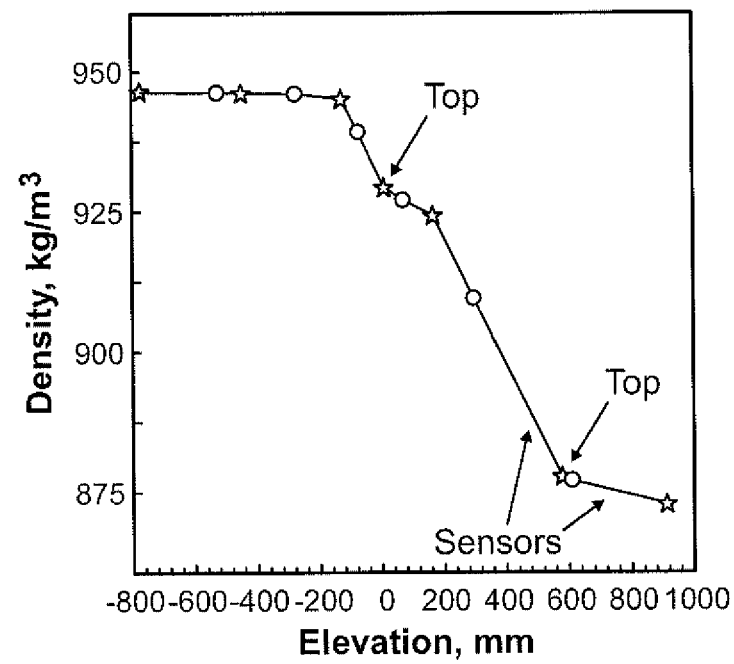
Figure 5:
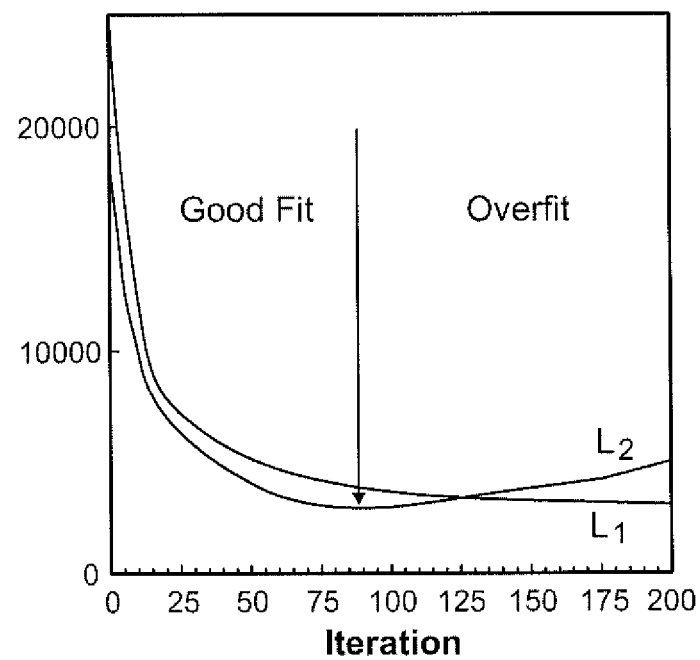
FIG. 5 illustrates an evolution of functions $L_1$, $L_2$ during calibration methods disclosed herein.
Figure 6:
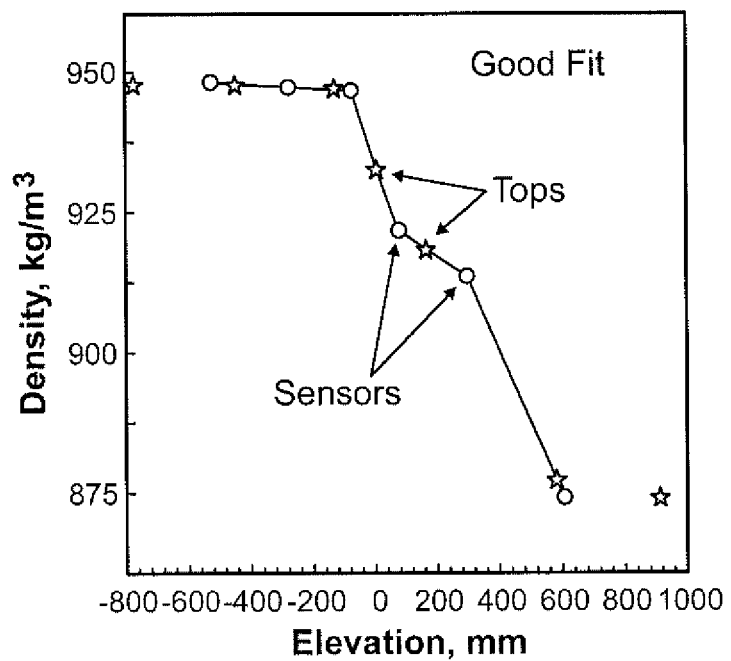
Figure 7A:
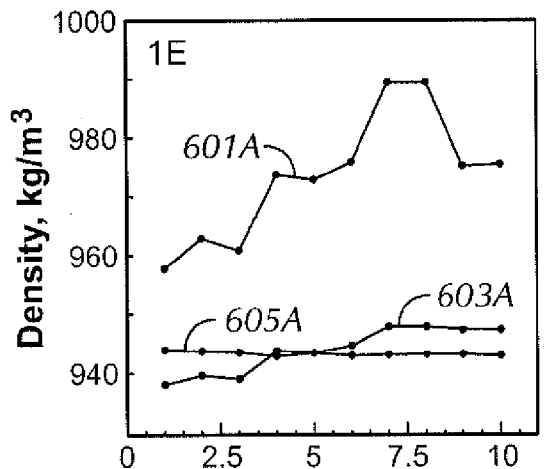
FIGS. 7A through 7D show a series of graphs illustrating the results of calibration in accordance with one or more embodiments of the present disclosure.
Figure 7B:
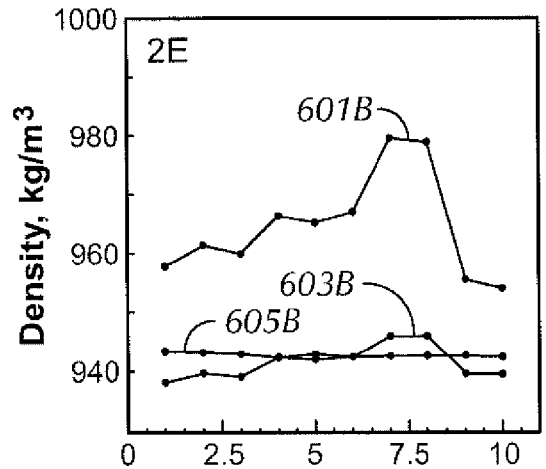
Figure 7C:
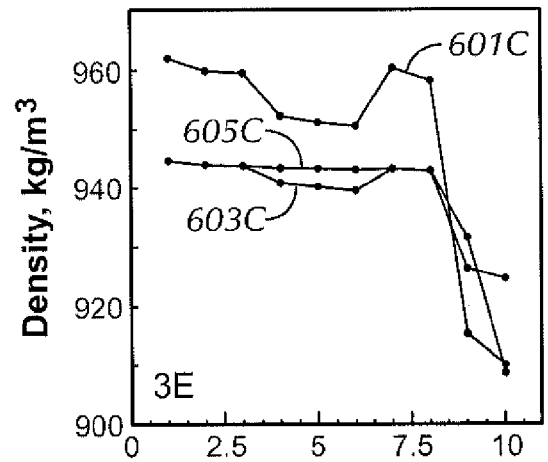
Figure 7D:
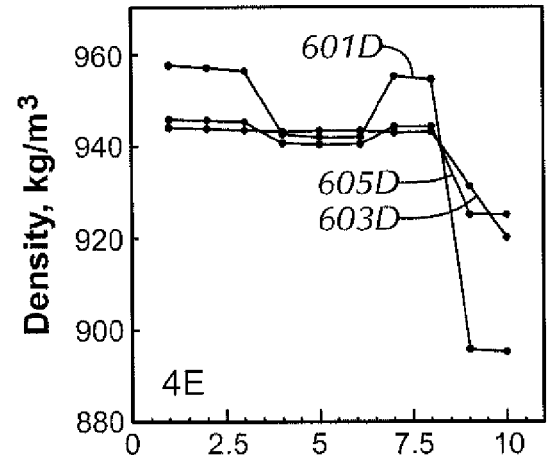
Figure 8A:
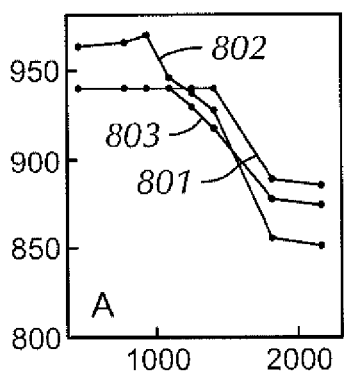
FIGS. 8A through 8I illustrate the density profiles for the events illustrated in FIGS. 7A through 7D.
Figure 8B:
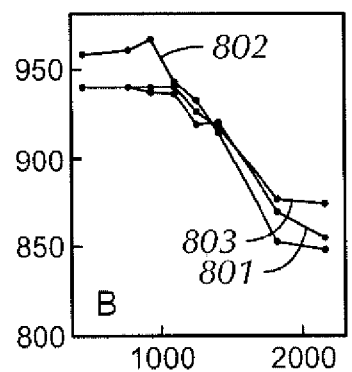
Figure 8C:
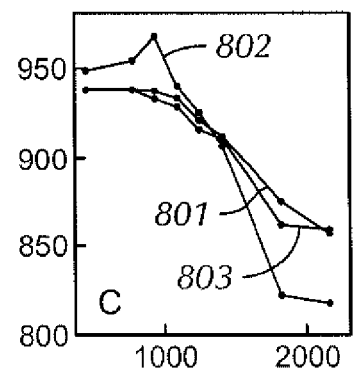
Figure 8D:
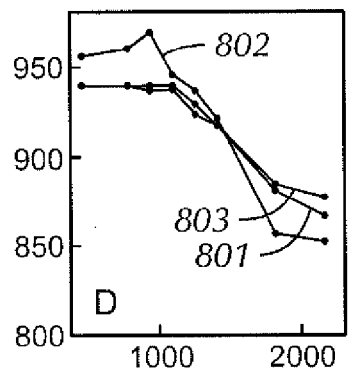
Figure 8E:
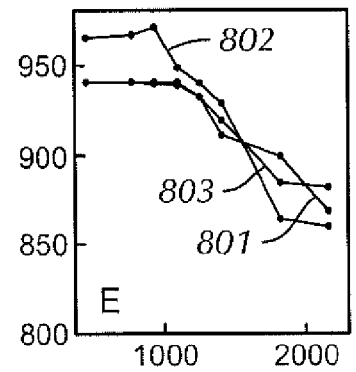
Figure 8F:
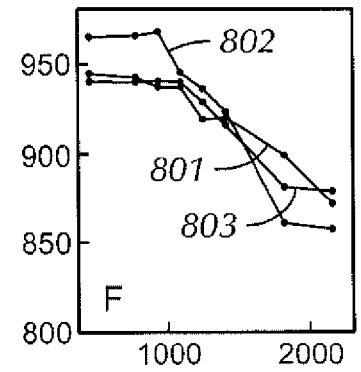
Figure 8G:
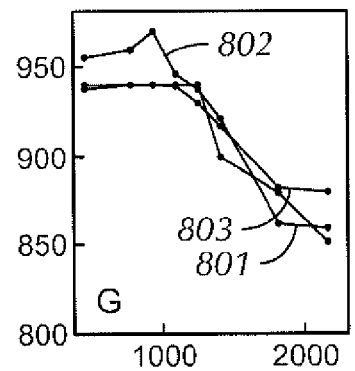
Figure 8H:
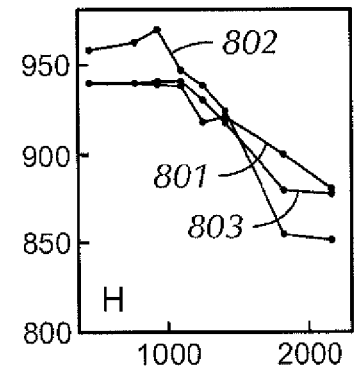
Figure 8I:
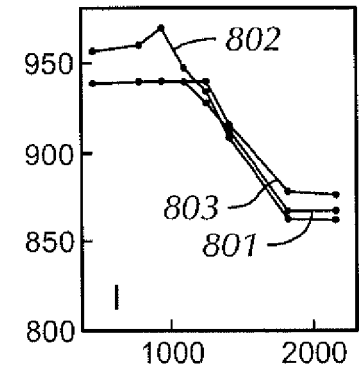

As described above, the tap densities $t_{ip}$ may be obtained by interpolation between the nodes derived from sensors' responses $s_{jp}$. However, in this example, as this resulted in an overfitting issue, a backwards procedure may be introduced. Specifically, as shown in FIG. 4, sensor responses $s_{jp}$* may be obtained by interpolation between the lab-reported tap densities $l_{ip}$ and comparing $s*_{jp}$ to actual responses $s_{jp}$. As minimization of $L_1$ proceeds, the value $$L_2 = \sum_{jp} \left( s_{jp}(\overline{s_0}, \overline{C}, \overline{C^*}) - s^*_{jp} \right)^2$$

is continuously monitored and minimization stops upon reaching the minimum of $L_2$. FIG. 5 shows the evolution of $L_1$ and $L_2$ throughout the process. At some point, $L_2$ passes its minimum while $L_1$ keeps attempting to approach a minimum. After that point, further reduction of $L_1$ is a deception as the model is overfitting to the specific dataset rather than learning a general trend for the density of the fluids encountered. The result with the minimization stopped upon reaching the minimum of $L_2$, as described above, is shown in FIG. 6. As compared to FIG. 3, this result remedies to overfitting trend and is a much more reasonable and proper trend. In this example, a similar result may also be obtained by direct minimization of $L_2$.

Example

As an example, a vessel having a density profiler sensor system and four sample ports was self-calibrated according to embodiments herein. FIG. 7 (A-D) shows a series of graphs which represent the performance of the calibration techniques in accordance with one or more embodiments of the present disclosure.

The initial calibration, lines 601A, 601B, 601C, and 601D proved inaccurate. Data obtained during regular non-interrupted operation have been used to improve the calibration.

These data contain 9 sampling events. Each event has 4 densities at 8 sampling ports (taps). 8 densities obtained from samples at 8 taps and 6 densities reported by the density profiler. In FIGS. 7A-D, the densities for the respective ports are plotted against sample number (1 through 10) elevation. Lines 601A, 601B, 601C, and 601D are the densities measured with initial calibration. Lines 603A, 603B, 603C, and 603D are the sensor densities as measured following self-calibration method in accordance with one or more embodiments of the present disclosure. Lines 605A, 605B, 605C, and 605D are the measured densities from the lab reports and are considered to be the most accurate densities. The improvement in the sensor measurement following self-calibration according to embodiments herein is considerable. FIGS. 8A through 8I illustrate the density profiles for the events illustrated in FIGS. 7A through 7D, including the laboratory values (801), reconstruction before calibration (802), and reconstruction after calibration (803).

As described above, embodiments disclosed herein provide for self-calibration of a density profiler. Self-calibration may advantageously provide for improved accuracy of the sensor density measurements, as well as for improving such measurements without the need to shut down operation of the vessel for re-calibration.

Advantageously, one or more embodiments of the present disclosure can effectively monitor and calibrate the sensor response throughout operation without the need to halt production. In addition, the method and apparatus may be effectively used to refine and maintain the accuracy of the sensor response through successive iterations. Effectively maintaining the accuracy of the sensor response without having to resort to a 2-point technique allows for a more efficient downstream process and continuous production. Further, those skilled in the art will appreciate that embodiments of the present disclosure can be implemented in various environments or applications.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for self-calibration of a density profiler, the process comprising:
measuring a density profile of a fluid in a vessel using a plurality of sensors;
measuring a density profile of the fluid in the vessel using a plurality of sample ports used to extract a sample of the fluid from the vessel;
interpolating a density of the fluid proximate a location of at least one of the plurality of sample ports based on the sensor measured density profile;
interpolating a density of the fluid proximate a location of at least one of the plurality of sensors based on the sample port measured density profile; and
adjusting a calibration of at least one of the plurality of sensors based on both the interpolated sample port density and the interpolated sensor density.

2. The process of claim 1, further comprising:
minimizing a first error function based on an initial sensor calibration constant, the measured sample port density profile and the interpolated sample port density to determine a current calibration constant; and
calculating a second error function based on an initial sensor calibration constant, the measured sensor density profile, the interpolated sensor density, and the determined current calibration constant.

3. The process of claim 2, further comprising:
iteratively minimizing the first error function and calculating the second error function; and
halting the iterative process upon reaching a minimum in the second error function.

4. The process of claim 3, wherein the adjusting a calibration of at least one of the plurality of sensors comprises:
adjusting a calibration constant of a sensor to the current calibration constant determined when the second error function reached a minimum.

5. The process of claim 2, wherein the first error function is represented by the equation:

$$L_1 = \sum_{p=1}^{n} \sum_{i=1}^{m} \left[ t_{ip}(\vec{s}_0, \vec{C}_0, \vec{C}) - l_{ip} \right]^2$$

where m is a number of sample ports analyzed n times, t is an interpolated sample port density, l is a measured sample port density, $\vec{s}_0$ is an initial sensor density, $\vec{C}_0$ is an initial calibration constant, and $\vec{C}$ is the current calibration constant.

6. The process of claim 2, wherein the second error function is represented by the equation:

$$L_2 = \sum_{jp} \left( s_{jp}(\vec{s}_0, \vec{C}, \vec{C}^*) - s_{jp}^* \right)^2$$

where j is a number of sample ports analyzed p times, s is a measured sensor density, s* is an interpolated sensor density, $\vec{s}_0$ is an initial sensor density, $\vec{C}$ is the current calibration constant, and $\vec{C}^*$ is a model calibration constant.

7. The process of claim 2, further comprising:
storing a history of the sensor measured density profile in a data store, wherein the sensor history includes one or more of a sensor identifier, a sensor location or height, a time stamp, and at least one of an initial sensor calibration constant, a sensor voltage counting rate output value, and a sensor density measurement value;
inputting a history of the sample port measured density profile in the data store, wherein the sample port history includes one or more of a sample port identifier, a sample port location or height, a time stamp, and a measured density value.

8. The process of claim 7, further comprising:
matching a time stamp of the sample port history to a time stamp of the sensor history.

9. The process of claim 7, further comprising repeating the measuring a density profile with sensors, the measuring a density profile with sample ports, the minimizing a first error function, and the calculating a second error function to determine new calibration constants for the plurality of sensors.

10. A system for self-calibration of a density profiler, the system comprising:
a plurality of sensors for measuring a density profile of a fluid in a vessel;
a plurality of sample ports for measuring a density profile of the fluid in the vessel, wherein the sample ports are used to extract a sample of the fluid from the vessel; and
a computer system configured to:
interpolate a density of the fluid proximate a location of at least one of the plurality of sample ports based on the sensor measured density profile;
interpolate a density of the fluid proximate a location of at least one of the plurality of sensors based on the sample port measured density profile; and
adjust a calibration of at least one of the plurality of sensors based on both the interpolated sample port density and the interpolated sensor density.

11. The system of claim 10, the computer system further configured to:
minimize a first error function based on an initial sensor calibration constant, the measured sample port density profile and the interpolated sample port density to determine a current calibration constant; and
calculate a second error function based on an initial sensor calibration constant, the measured sensor density profile, the interpolated sensor density, and the determined current calibration constant.

12. The system of claim 11, the computer system further configured to:
iteratively minimizing the first error function and calculating the second error function; and
halting the iterative process upon reaching a minimum in the second error function.

13. The system of claim 12, the computer system further configured to:
adjust a calibration constant of a sensor to the current calibration constant determined when the second error function reached a minimum.

14. The system of claim 10, further comprising:
a data store for storing a history of the sensor measured density profile and a history of the sample port measured density profile,
wherein the sensor history includes one or more of a sensor identifier, a sensor location or height, a time stamp, and at least one of an initial sensor calibration constant, a sensor voltage counting rate output value, and a sensor density measurement value, and
wherein the sample port history includes one or more of a sample port identifier, a sample port location or height, a time stamp, and a measured density value.

15. The system of claim 14, the computer system further configured to:
access the data store; and
match a time stamp of the sample port history to a time stamp of the sensor history.

16. The system of claim 10, wherein the plurality of sensors are located in a single detector apparatus.

* * * * *